(12) United States Patent
Fuentes

(10) Patent No.: US 7,338,055 B2
(45) Date of Patent: Mar. 4, 2008

(54) METHOD AND WORKSTATION FOR SINGLE PATIENT MEDICAL CARE

(76) Inventor: Carl Fuentes, 5000 K Ave., #4112, Plano, TX (US) 75074

( * ) Notice: Subject to any disclaimer, the term of this patent is extended or adjusted under 35 U.S.C. 154(b) by 474 days.

(21) Appl. No.: 10/610,939

(22) Filed: Jul. 1, 2003

(65) Prior Publication Data

US 2005/0001395 A1 Jan. 6, 2005

(51) Int. Cl.
*B62B 3/02* (2006.01)
(52) U.S. Cl. ............................ 280/79.3; 280/47.35
(58) Field of Classification Search ............ 280/47.35, 280/47.34, 79.11, 79.3, 79.2, 47.18, 47.19; 312/223.2, 223.3; 174/50; D24/234
See application file for complete search history.

(56) References Cited

U.S. PATENT DOCUMENTS

| | | | | |
|---|---|---|---|---|
| 2,620,251 A | * | 12/1952 | Restivo | 312/240 |
| 3,336,855 A | * | 8/1967 | Messina | 454/60 |
| 3,997,218 A | * | 12/1976 | Wolf et al. | 312/209 |
| 4,114,965 A | * | 9/1978 | Oye et al. | 312/209 |
| 4,193,650 A | * | 3/1980 | Gray et al. | 312/205 |
| 4,681,378 A | * | 7/1987 | Hellman, III | 312/223.2 |
| 5,016,948 A | * | 5/1991 | Welch et al. | 312/249.12 |
| 5,165,770 A | * | 11/1992 | Hahn | 312/265.4 |
| 5,290,058 A | * | 3/1994 | Adams et al. | 280/651 |
| 5,399,007 A | * | 3/1995 | Marconet | 312/209 |
| 5,518,310 A | * | 5/1996 | Ellman et al. | 312/249.12 |
| 5,765,842 A | * | 6/1998 | Phaneuf et al. | 280/47.35 |
| 5,887,878 A | * | 3/1999 | Tisbo et al. | 280/47.19 |
| 6,022,088 A | * | 2/2000 | Metzler | 312/209 |
| 6,102,497 A | * | 8/2000 | Ehr et al. | 312/209 |
| 6,359,217 B1 | * | 3/2002 | Thompson et al. | 174/50 |
| 6,384,380 B1 | * | 5/2002 | Faries et al. | 219/385 |
| 6,493,220 B1 | * | 12/2002 | Clark et al. | 361/686 |
| 6,565,166 B1 | * | 5/2003 | Bulk et al. | 312/257.1 |
| 6,626,445 B2 | * | 9/2003 | Murphy et al. | 280/47.34 |
| 6,663,202 B2 | * | 12/2003 | Spann | 312/249.12 |

\* cited by examiner

*Primary Examiner*—Jeff Restifo
(74) *Attorney, Agent, or Firm*—Darcell Walker

(57) ABSTRACT

A reconfigurable medical workstation enables efficient arrangement of medical equipment used to provide care to a specific patient. The workstation contains a comportment space that can be divided into compartments as needed to house the medical equipment. The compartment configurations can be uniquely created to house the specific medical equipment for the patient. Because the needs of patients are different and require different kinds of medical equipment the compartment configuration for one patient can be different in the present invention from the compartment configuration for another patient.

12 Claims, 6 Drawing Sheets

METHOD AND WORKSTATION FOR SINGLE PATIENT MEDICAL CARE

FIELD OF THE INVENTION

The present invention relates to a method and device for providing care to a medical patient and in particular to method and device for efficiently arranging medical equipment when providing healthcare to a patient and more particular to a reconfigurable device and a method for configuring the device such that medical equipment can be uniquely and specifically arranged and stored in the device in order to provide more efficient and effective healthcare to a patient.

BACKGROUND OF THE INVENTION

A home healthcare system is necessary for a patient requiring substantial healthcare once the patient is discharged from a hospital. Home healthcare systems include numerous pieces of medical equipment (durable medical equipment examples—heart monitors, pulse oximeter, aspirator, feeding pumps, nebulizers, ventilators etc. large amounts of medical supplies examples (syringes, suction catheters, respiratory supplies, bandages, trachs, tongue blades etc). patients requiring the need to store and secure wide assortment of medical prescription drugs.

When a medically fragile patient is released from the hospital they usually do so with the understanding that they are not cured of their illness or they haven't fully recovered from their injuries, but are stable enough to be cared for in a home environment. These people are still patients and in many cases they require the same medical equipment, supplies and treatment that they where receiving in the hospital. In many cases, family members are sent home with little or no medical training to care for loved ones. To ease the transition from the hospital to home, a patients' doctor may order that they receive a certain number of nursing hours at home. These hours are to be provided by a licensed home health nursing agency or licensed RN or LVN. Upon the patients' arrival home, the medical supply company sends a RN to the home to teach the patient and their family members how to operate and use the medical equipment and supplies. This is where the problem begins.

Over the years, advances in medical treatment, equipment technology and devices have allowed patients that only a few decades ago would have died in the hospital, can now be cared for in a home setting. While families and patients are thankful for these advances, the problem is the home is not a hospital. Many medically fragile patients are sent home with three, four, five and sometimes more pieces of medical equipment, which must be placed within close proximity of the patient. In every single case this scenario poses a problem for which there is currently no solution.

Human factors are a discipline that focuses on those variables that affect the performance of individuals using equipment. Errors in the use of medical devices are often caused, at least in part, by the design of the user interface, i.e., those features which healthcare practitioners and patients or family members interact. Mistakes made during device operation not only can hamper effective patient treatment, monitoring, or diagnosis but also in some cases can lead to injury or death. The factors that immediately come into play include patient, nurse and caregiver safety, the ability to reach and accurately set the controls of equipment in a safe and timely manner, the ability to read visual displays and monitors, and the ability to hear the audio alarms of the equipment being used. Power outages, accidental unplugging of equipment (in some cases this equipment is mission critical i.e. ventilators), insufficient outlets, the equipments own electrical cord and in many cases extension cords reaching from across the room creating certain trip hazards further compound problems.

Another problem caused by the use of medical equipment in patient care is the leads (wiring) and tubing connecting the equipment to the patient. Again, this scenario poses a problem for which there is currently no solution. Here is one example. In a home health setting, more often than not, electrical cords from the medical equipment become entangled with the O2, suction, feeding tubing and leads (wiring) that are connected to the patient. This poses several problems of immediate concern.

1. Many times quick reaction to a patients needs are of critical importance. It is not helpful in that critical moment to have to decipher which is an electrical cord and which is a lead or tubing. In fact tubing can become so tangled it is often hard to distinguish which tube is O2, the nebulizer tubing, or the suction tubing.
2. Nurses or caregivers while administering care or by the patient's movement i.e. shifting positions in bed or getting out of bed often pulls medical equipment off shelving or tables. Often, falling equipment breaks or disconnects the leads and pulls tubing out or away from the patient rendering it ineffective.
3. Because there is no effective way of storing suction, I.V., feeding, breathing tubing and monitoring leads while not in use, they sometimes fall to the floor rendering them not sterile and they must be prematurely cleaned or replaced. Not only is this a safety issue but also it is a waste of time and money.
4. In many home health scenarios, lack of space and electrical outlets are pressing issues; therefore equipment must be placed on both sides of the bed. This causes several problems that must be addressed. First, when equipment is on both sides of the bed, it becomes very difficult to move the patient. Tubing and leads are only so long and any movement to one side of the bed or the other usually pulls equipment on the other side of the bed off the table. Secondly, it's very hard to visually monitor and reach equipment controls, which are prescribed to be used as a unit, when some equipment is on the other side of the bed from which you are working.
5. Tubing and wiring can often become kinked or twisted restricting oxygen flow or causing electrical interference.

The fact that these patients have so many pieces of medical equipment reduces patient mobility and usually means that the patient is confined to a single room. As a result of this confinement, the patient is denied the opportunity to interact with the rest of the family. Patient interaction with the rest of the family is well documented in medical journals as a factor in overall patient comfort and speed of recovery.

In addition, families with small children often battle to keep the children from playing with the medical equipment. The equipment is sometimes turned off and settings are often compromised without the knowledge of the parent. Furthermore, most of these patients have many prescription medications and families are often forced to hide medication to keep it out of reach of the children.

Medically fragile patients require a huge amount of medical supplies and because the baseline (normal state of health) of medically fragile patients can go for stable to critical in a matter of minutes, having supplies within close reach is extremely important. The following scenario is one where policy and procedure mandate that these supplies be close to the patient. When a patient has a tracheotomy it is mandated that a replacement trach of the same size and one the next size smaller be placed next to the patient. An example would be a Shiley Ped 4.0 and a Shiley Ped 3.5. This is usually accomplished by taping the trachs either to the bed or the wall. The problem with this practice is that on some occasions the tape doesn't hold and the trachs end up falling on the floor or behind the bed making a quick trach replacement impossible. At times a patients' trach may become plugged by mucus secretion and may require immediate removal and replacement. The process of changing a trach in a timely manner requires that a suction machine, O2 supply, pulse oximeter and medical supplies, such as, sterile gloves, lubricating jelly, trach ties, sterile gauze or wipes and suction catheters, all be within easy reach of the nurse or caregiver. In a home health setting this is usually easier said than done.

It is a well-known fact that in order to care for medically fragile patients, very strict policies and procedures mandate the physician's orders be followed very closely. Medication, therapy schedules and physician ordered medical equipment and medical supplies all must work in unison in order for a nurse or caregiver to provide the patient with the highest level of recovery, comfort and independence.

There remains a need for a method and system that can provide for more efficient arrangement of medical equipment when providing health care so that the care giver can more easily and efficiently access the medical equipment and provide the necessary care to the patient.

SUMMARY OF THE INVENTION

It is an objective of the present invention to provide a single point of care for a caregiver when attending to the needs of a patient.

It is a second objective of the present invention to provide a reconfigurable medical workstation that can be specifically configured to meet the unique needs of a patient.

It is a third objective of the present invention to provide a reconfigurable medical workstation that can be specifically configured to house the specific medical equipment needed by a particular patient.

It is a fourth objective of the present invention to provide a medical workstation that can increase patient mobility and patient interaction with other people.

It is a fifth objective of the present invention to provide a medical workstation that can increase the efficiency in arranging patient equipment around the patient receiving the medical care.

It is a sixth objective of the present invention to provide a medical workstation that can enable a caregiver to have easier access to medical equipment used to provide care to the patient.

The present invention provides a reconfigurable medical workstation that can enable efficient arrangement of medical equipment used to provide care to a specific patient. The workstation contains a comportment space that can be divided into compartments as needed to house the medical equipment. The compartment configurations can be uniquely created to house the specific medical equipment for the patient. Because the needs of patients are different and require different kinds of medical equipment the compartment configuration for one patient can be different in the present invention from the compartment configuration for another patient. Current medical cabinets do not provide compartments to store different equipment for different patients. Any equipment stored in these cabinets is standard equipment used for any patient.

The present invention is a multi-task, single patient medical workstation designed for use in hospital and home health environments. The present invention provides an alternative to the single-task and outdated design and appearance of standard medical cabinets, carts and IV poles. The versatile design of the workstation addresses a multitude of documented safety concerns, while assisting nurses and caregivers with the task of caring for patients with multiple pieces of medical equipment and large amounts of medical supplies. This workstation can be manufactured in any dimensions, but the combination of organization, accessibility, safety, mobility, a medical equipment platform, the ability to store all of the patient's immediate medical supplies and medications are the factors that contribute to the design of the workstations. Using the present invention as the platform from which all the patient's care can be delivered creates a strategy, which is a step in a new direction for nurses and caregivers working at patient bedsides. The primary benefits of this invention are as follows: 1) The creation of a single point of care; 2) Patient mobility; and 3) Patient and caregiver ergonomics.

In the creation of a single point of care, the underlying philosophy in the design of this workstation is to position all the of the patient's medical equipment and supplies on a single side of the bed, in a forward position and within arms reach of the patient point of care, point of care meaning 'the location at which patient services are delivered'. With this strategy in place all interaction between the nurse and a patient's equipment and supplies and the nurse and the patient can be accomplished from a 4' by 4' work area located directly in front of the workstation and at one side of the patient's bed. With all the patients equipment stationed on one side of the bed, the other side of the bed is now clutter free, creating an area in which a second nurse can quickly be in position to assist the lead nurse without fear of accidentally unplugging equipment or disengaging patient leads or tubing while repositioning equipment in order to get to the patients bedside.

Patient mobility is an extremely important issue when caring medically fragile patients. Patient interaction with the rest of the family is well documented in medical journals as a factor in overall patient comfort and speed of recovery. The single patient medical workstation provides a solution to this pressing issue. The fact that medically fragile patients have so many pieces of medical equipment and supplies reduces patient mobility and usually means they are confined to a single room and are denied the opportunity to interact with the rest of the family. The fact that all of the patients equipment and supplies are in single unit allows patient and their equipment and supplies to easily be moved from room to room. It is no long necessary for nurses or caregivers to unplug and move each individual piece of equipment from one room to the other and then try to find shelf space and a sufficient number of power outlets within the room. Unplug one power cord; move the workstation where you like and plug it back in—that's it. Each workstation is mounted on four six-inch semi-pneumatic heavy-duty swivel castors, which provide maximum stability and excellent maneuverability making the single patient medical workstation highly mobile. Unplug one power cord; move it where you like and plug it back in—that's it. Each workstation can be pulled and maneuvered by a wooden handle located on the left and right sidewall of the workstation and secured the height between the medical equipment platform and the medical supply and medication storage compartment. The handle connected to the work tray also serves as the steering mechanism when in its pulled out position. The users hand can easily pass through each handle allowing the user the ability to maneuver the workstation with ease. On the top surface of the each handle a grove has been routered into the handle on each side of the grip allowing the user a place store writing utensils. The swing lock enable it to be move while closed, preventing the shelf from sliding out while pulling the unit. A handle in front of the unit is being implemented within the accent wood piece for future units.

Ergonomics is a very pressing issue in the healthcare industry and the Osha mandates and enforces the regulation and policies that are in place. Healthcare workers perform a variety of physical tasks during the course of the day while caring for medically fragile patients. Performing these tasks requires healthcare workers to do a lot of standing, sitting, reaching, turning, lifting, pushing and pulling. If these tasks are performed with proper body alignment and movement the work will be easier. Maintaining good posture through proper body alignment allows one to maintain balance and reduces muscle strain by distributing the total body weight around a central point called the center of gravity. The philosophy of a single point of care, which is made possible by the single patient medical workstation, allowing the healthcare worker to perform the tasks while standing in a 4' by 4' area.

With the present invention, when there is a determination of the particular treatment for a patient and a determination of the equipment that the patient will need, a unique compartment configuration is generated for the workstation of the present invention. The number and size of the compartments is determined based the particular equipment needed by the patient. At this point, the workstation is configured in accordance with that determined configuration.

DETAILED DESCRIPTION OF THE INVENTION

Figure 1:
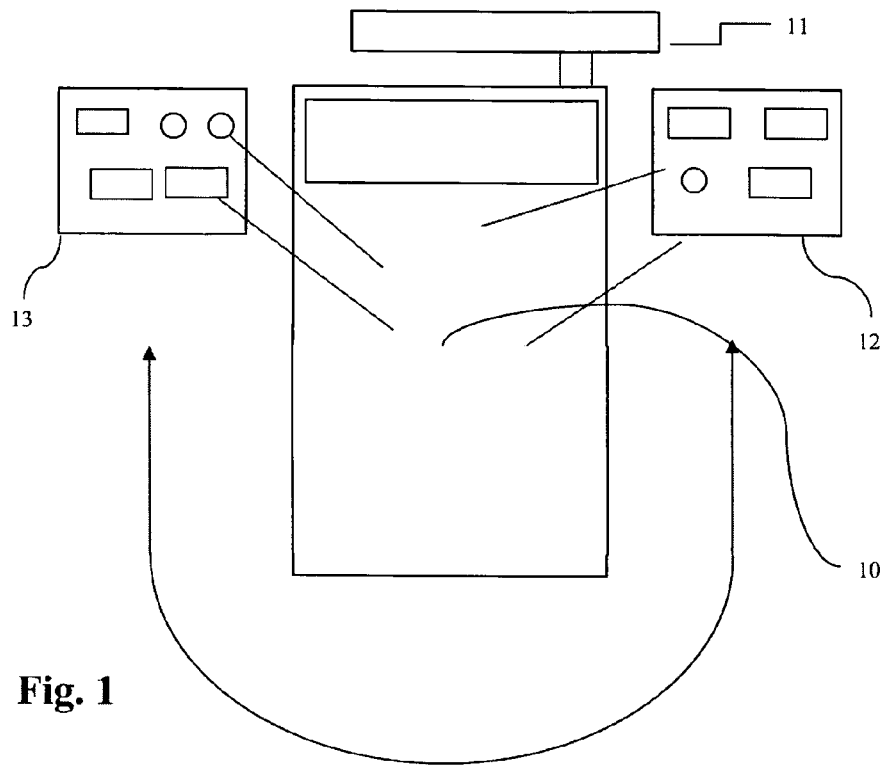
FIG. 1 is a view of a floor arrangement of a typical patient room showing medical equipment on both sides of the patient's bed.

FIG. 1 illustrates serious problem with the current way that most health care is administered today. In a typical patient room, there is a bed 10 and a wall panel 11. The wall panel can contain covers for vents that lead to central resources for air of essentials needed by a patient. Also included in a patient's room two table surfaces 12 and 13 that contain various pieces of medical equipment for the patient. The arrow indicates the path traveled by a caregiver during the process of administering to the patient. As shown, the caregiver has to cover a substantial area moving between two sets of equipment on each side of the bed. Some patient rooms may only have one surface for equipment and medicine, however in these cases some equipment is usually hanging from the I.V. pole. Furthermore, there is still equipment on both sides of the patient. When there is only one caregiver (which is usually the case especially in a home healthcare environment) and an emergency develops, there is potential for a serious problem when the caregiver needs to simultaneously access two different pieces of equipment that are one opposite sides of a patient. As shown, the time required by the caregiver to travel from one side of the bed to the other side may crucial in an emergency situation. In addition, in non-emergency situations, the random arrangement of equipment on the surfaces leads to inefficient care and the potential for mistakes in administering the health care.

Figure 2:
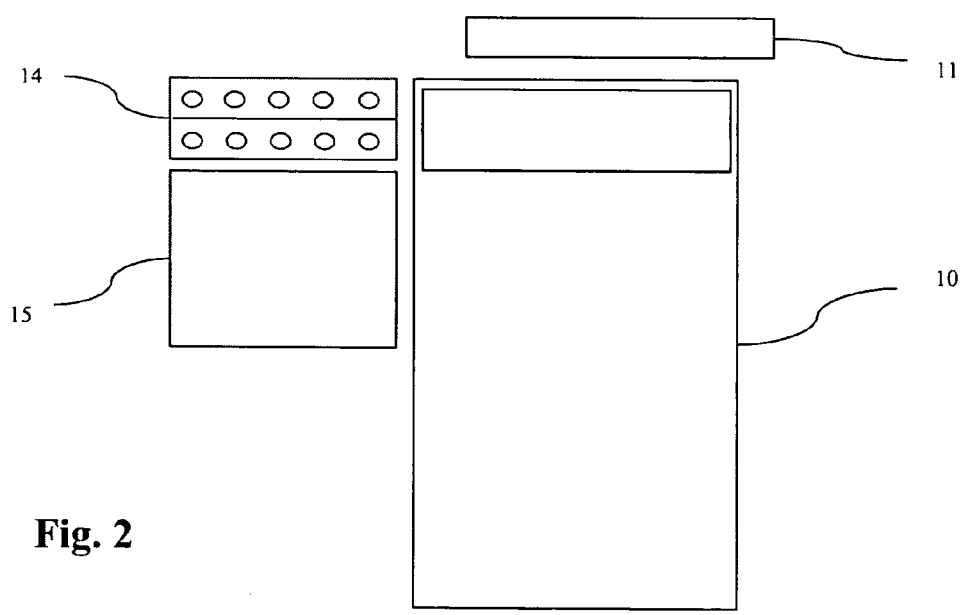
FIG. 2 is a view of a floor arrangement of a patient room in accordance with the present invention showing all of the medical equipment on one side of the patient's bed.

FIG. 2 shows the resulting arrangement of a patient's room when the present invention is used to contain the medical equipment needed by the patient. As shown, all of the equipment is contained on one side of the patient's bed in a device 14 of the present invention. The caregiver has access to most if not all of the equipment. The equipment is arranged in a predetermined configuration based on the needs of the patient. As shown, the work area 15 for the caregiver is substantially smaller in this case.

The underlying philosophy in the design of the workstation is to position all the of the patient's medical equipment and supplies on a single side of the bed, in a forward position and within arms reach of the patient point of care, point of care meaning 'the location at which patient services are delivered'. With this strategy in place all interaction between the nurse and a patient's equipment and supplies and the nurse and the patient can be accomplished from a 4' by 4' work area located directly in front of the workstation and at one side of the patient's bed. With all the patients equipment stationed on one side of the bed, the other side of the bed is now clutter free, creating an area in which a second nurse can quickly be in position to assist the lead nurse without fear of accidentally unplugging equipment or disengaging patient leads or tubing while repositioning equipment in order to get to the patients bedside.

Figure 3:
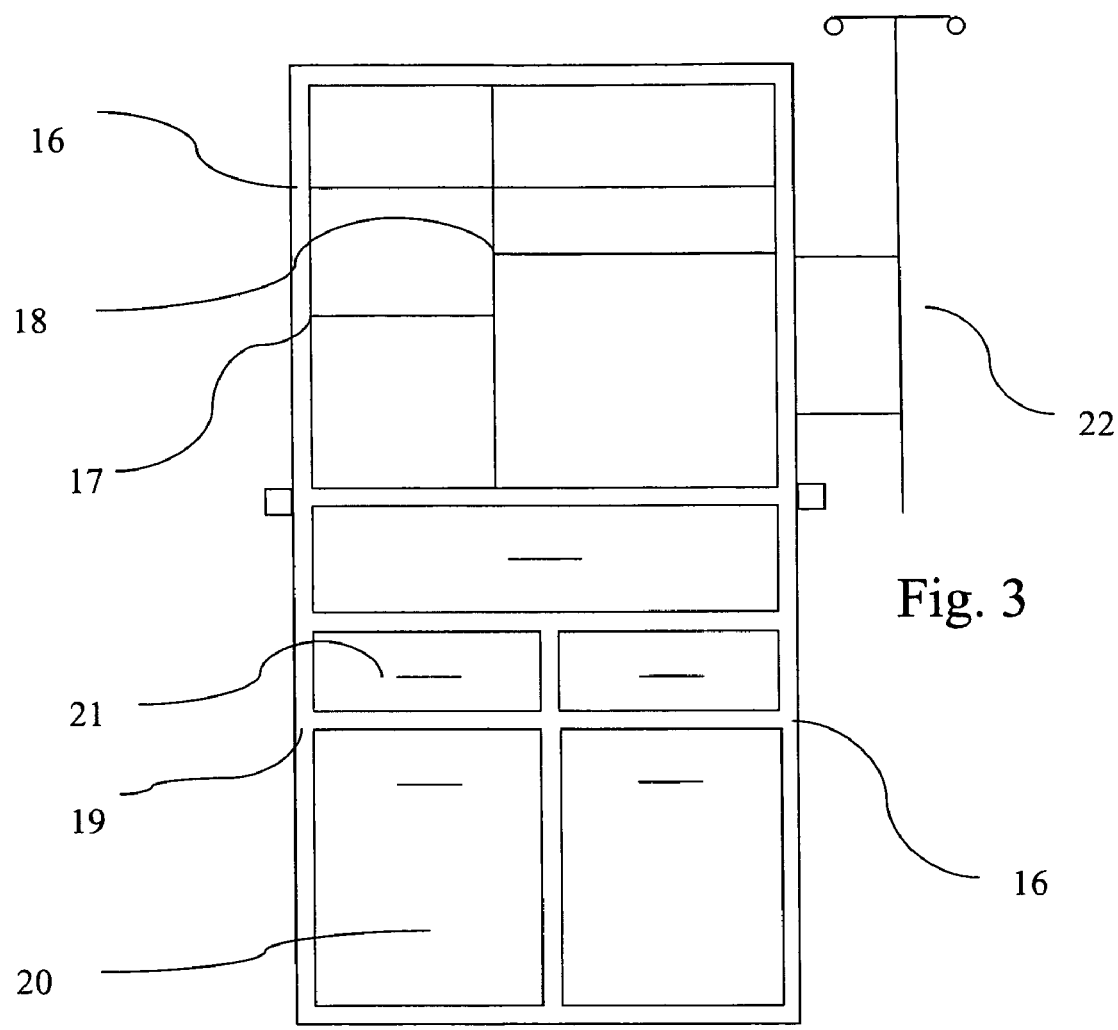
FIG. 3 is a front view of a configuration of the present invention showing an arrangement of storage compartments for storage of medical equipment.

FIG. 3 illustrates the primary features of the present invention. As shown, the invention gives the appearance of a typical cabinet for storing items. The compartment section 16 shows several compartments used for storing medical equipment. This section comprises several horizontal dividers 17. These dividers can be of different lengths as shown. Also shown is a vertical divider 18. FIG. 3 shows only one divider, however, different configurations can have more than one vertical divider and these dividers can also be of various lengths. The compartment sides have slots or holes for attaching the horizontal and vertical dividers. The vertical dividers and horizontal dividers can also have slots or holes for the same purpose. These dividers further contain pins for insertion into the slots for securing and supporting the dividers. The lower section 19 of the invention contains drawers 20 that can be used to store supplies or trash. Rollers on bottom of the invention facilitate mobility of the invention. Handles 21 between the upper and lower sections are used for retrieving a table surface stored between the upper and lowers sections of the invention. In addition, an I.V. pole 22 can be attached to the side to the invention.

Figure 4:
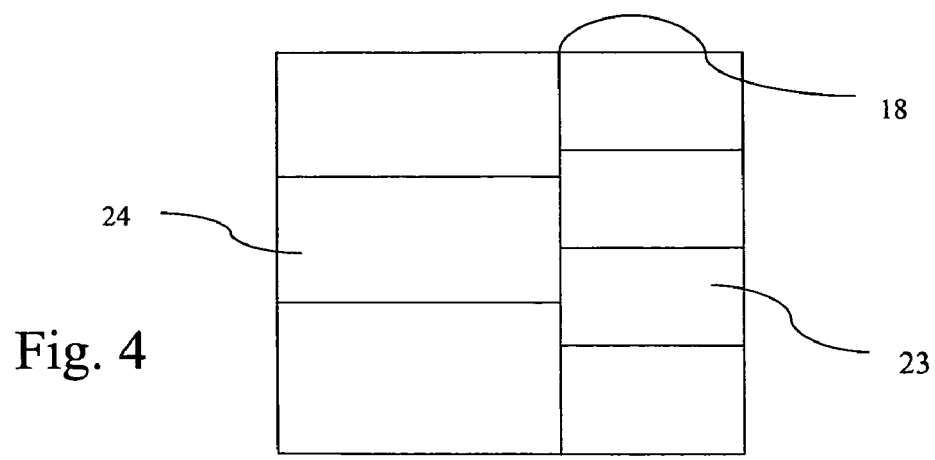
FIG. 4 is a front view of an alternate configuration of the storage compartments of the present invention.

FIG. 4 shows an alternate configuration of the compartment section of the invention. In this embodiment, the vertical divider 18 is in a different location in the compartment. In addition, the compartments 23 and 24 are different in number and in size. As mentioned, the different compartment configurations are based on the specific equipment needs of the patient.

Figure 5:
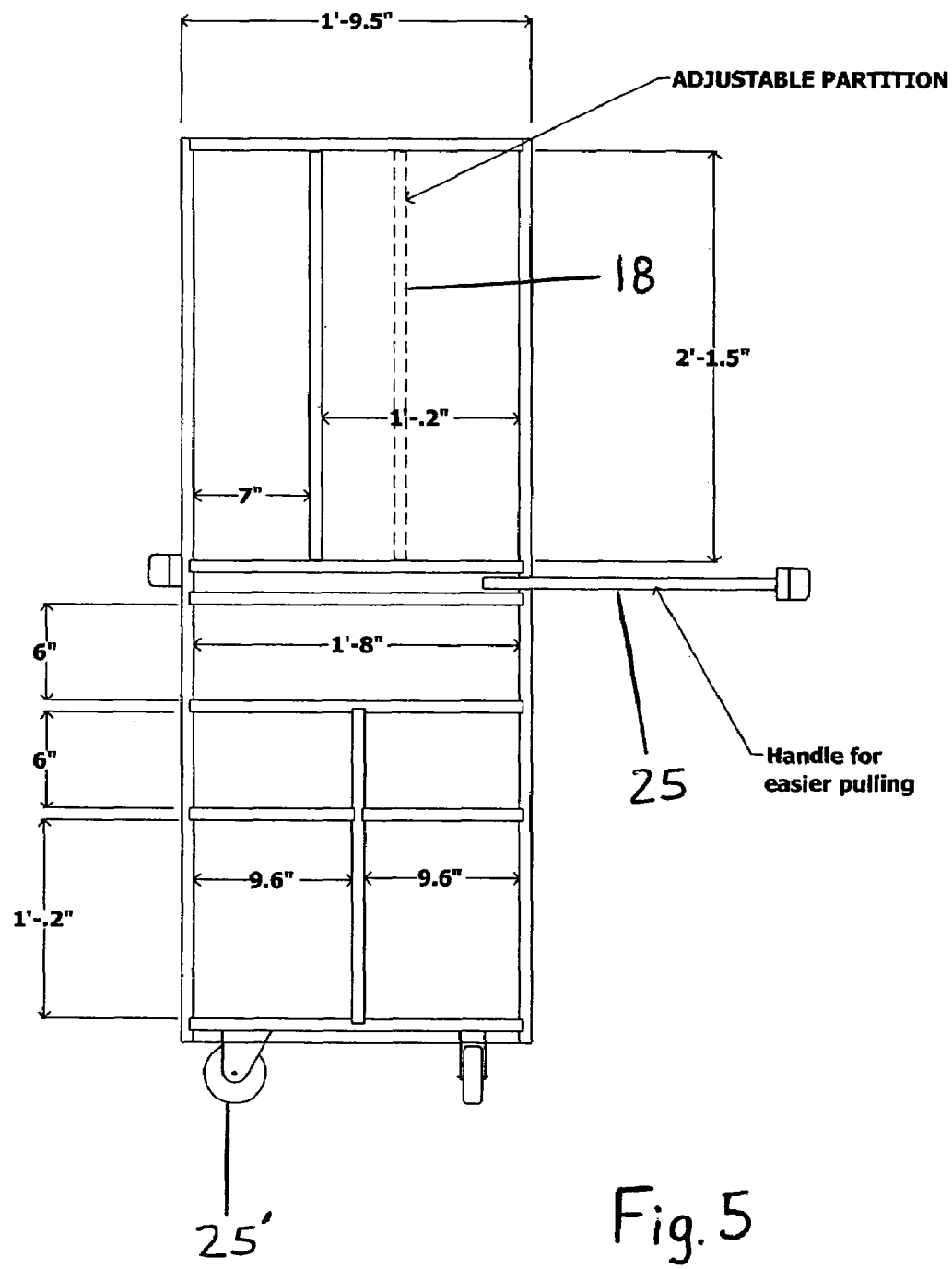
FIG. 5 is a front view of the present invention showing an adjustable partition and a sliding table surface.

FIG. 5 shows a view of the invention with an adjustable vertical divider 18. There can be more than one vertical divider. Also shown is the extended horizontal table surface 25 and rollers 25'.

Figure 6:
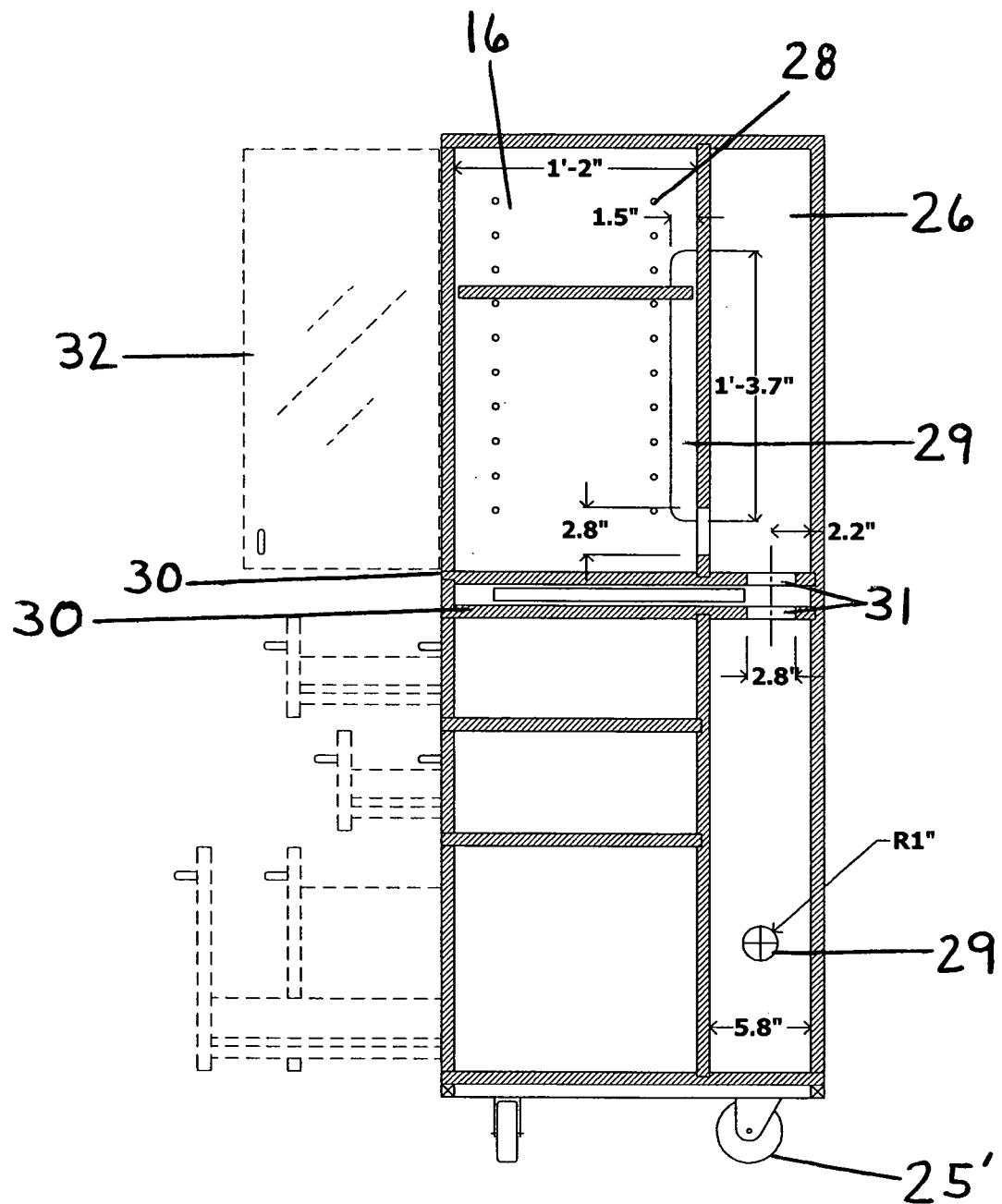
FIG. 6 is a side view of the present invention showing front and back compartments of the present invention.

FIG. 6 shows the side view of the invention. This view shows the back compartments 26 and 27 that contain the wires that connect the equipment to a power source. Also shown are holes 28 that allow for attachment of the horizontal dividers at various locations along the walls. Pins at the ends of the dividers are inserted into these holes to attach the dividers to the walls. Dividers can also have holes for attachment of other dividers. Both the holes and pins can have a material coating that will facilitate multiple insertions and withdrawal of the pins from the holes without wearing of the holes over long periods of insertions and withdrawals. An opening 29 provides for channeling the wiring from the front compartment to the back compartments. Middle dividers 30 have openings 31 for channeling the wiring between the back compartments. Also shown is glass door 32 covering the top front compartment 16. FIG. 6 also indicates preferred dimensions for the workstation.

Figure 7:
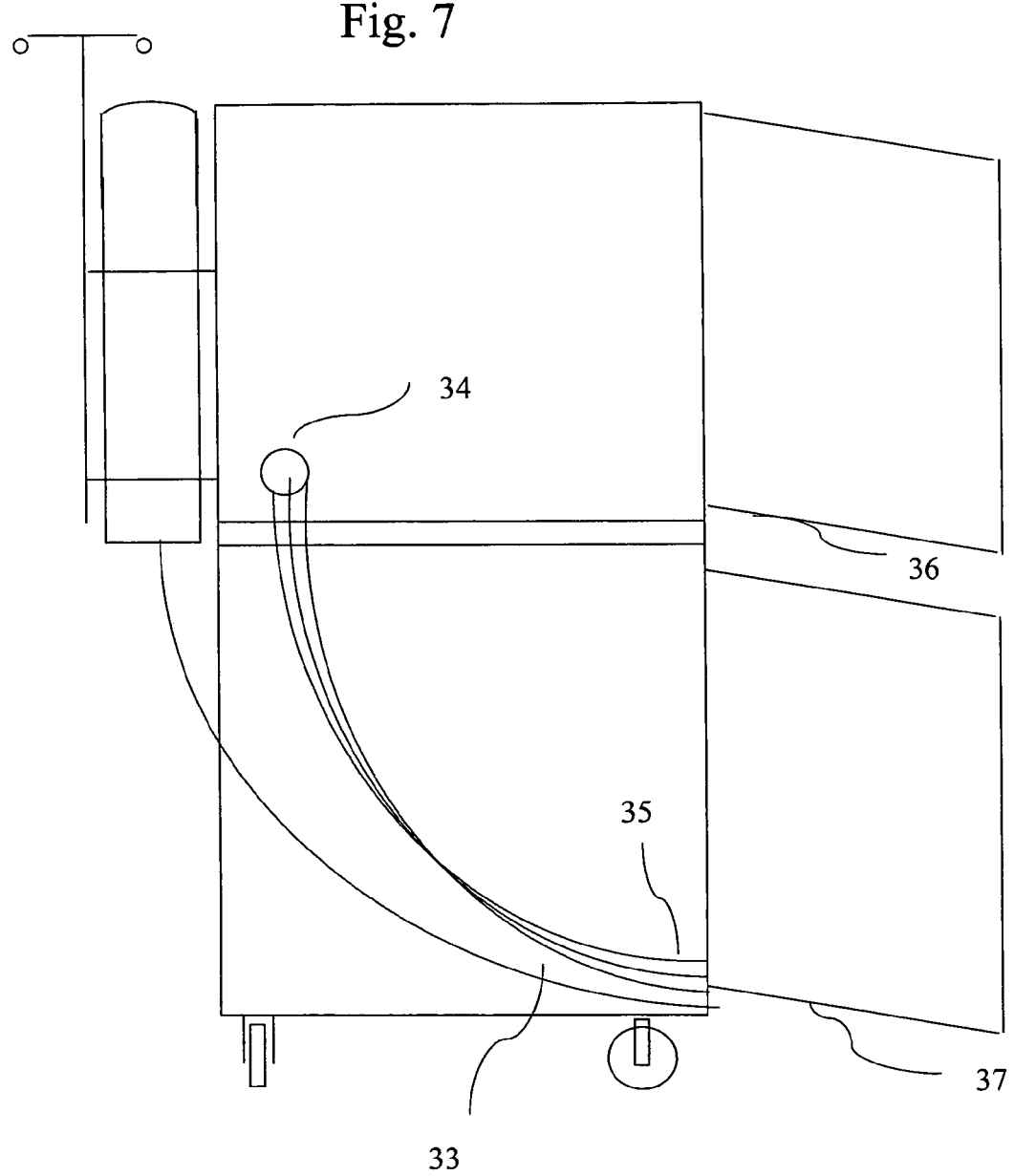
FIG. 7 is a back view of the invention showing top and bottom compartments for containing and channeling wiring from medical equipment contained in the front compartments of the present invention and equipment attached to the present invention.

FIG. 7 is a back view of the invention showing top and bottom compartments for containing and channeling wiring from medical equipment contained in the front compartments of the present invention and equipment attached to the present invention. As shown, wiring 33 from the medical equipment is channeled through an opening 34 in the upper section. The wiring extends through a second opening 35 in the lower section to a power supply. Doors 36 and 37 the back compartment of the invention to prevent entanglement of the medical personnel with the wiring.

Figure 8:
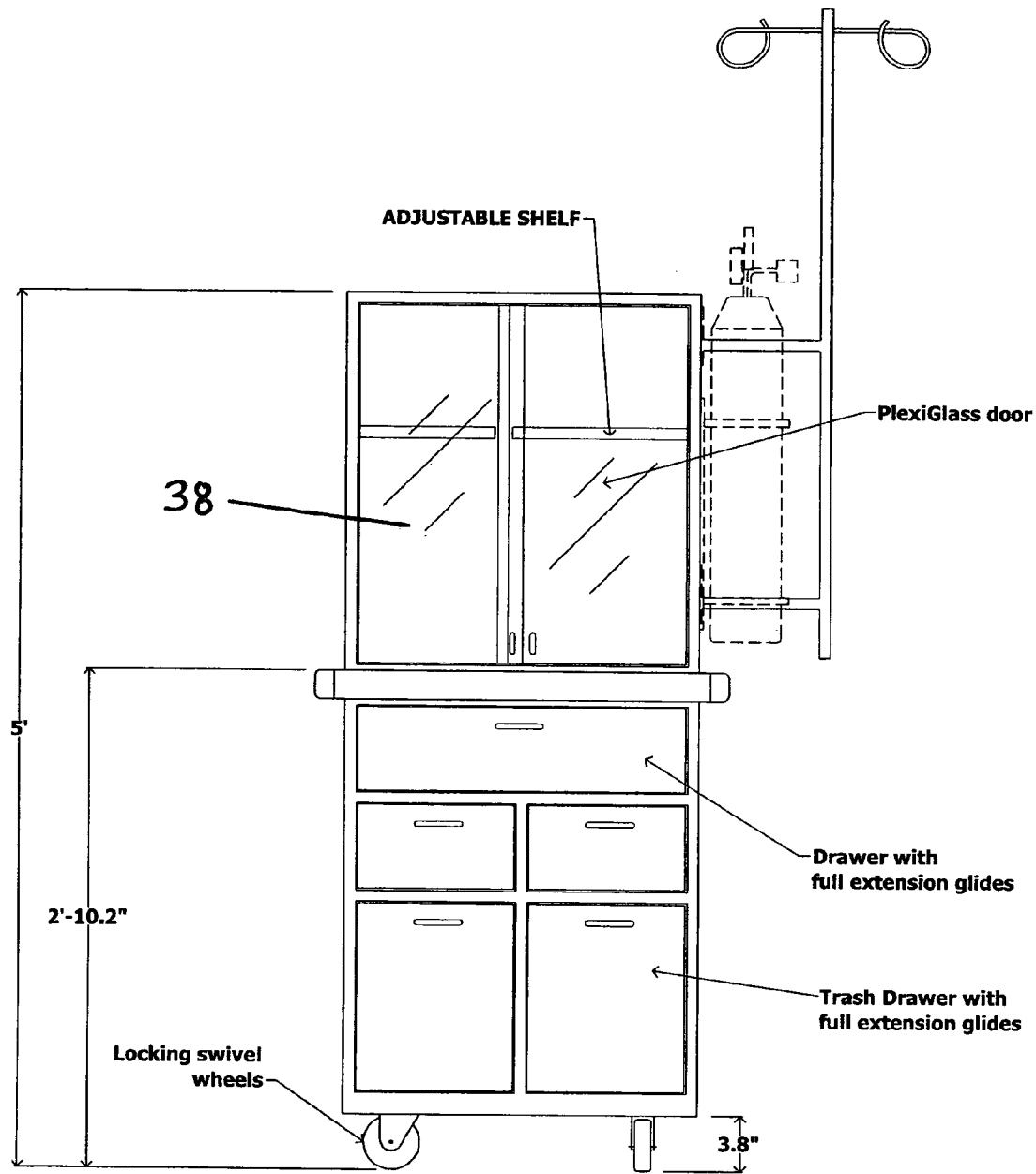
FIG. 8 shows a front view of the invention with an intravenous pole attached to the invention.

FIG. 8 shows a front elevation view of the present invention. This view is similar to FIG. 3. Shown are doors 38 that cover the front upper compartment of the present invention. These doors can be made of PlexiGlass or preferably some other transparent material. However, the material for the door does not need to be a transparent material. At this point, it is advantageous to further explain several aspects and features of the present invention.

Medical Equipment Platform

The medical equipment platform positions the patients' equipment at proper height to maximize the users ability to interact with the equipment and the patient at the same time. Medical equipment housed in the medical equipment compartment and can be visually monitored through two clear acrylic doors in the front of the cabinet allowing users to: quickly and properly identify controls, switches, and displays; reach and accurately set controls; read displays accurately; and associate controls with their related displays. This workstation design allows for a well-organized, self-contained and uncluttered arrangement of all the medical equipment required by a patient. To insure that the intensity and pitch of auditory signals can easily be heard the doors are positioned with a 0.25" gap around the entire opening including between the two doors.

The workstations of the present invention are designed so that the "medical equipment platform" can easily be reconfigured to new dimensions within seconds to accommodate the different medical equipment and supply scenarios for a variety of patients. This can be accomplished by removing the shelving and disengaging the center divider latch then shifting the center divider left or right from its current peg hole position, then reengaging the center divider latch and reinserting the shelving into their desired positions. Once the shelving is in its desired positions, the equipment is installed into the cabinet and onto shelving. The cords are then installed through the unshaped cut aways in the shelving, through the "round electrical cord portal" located in the center wall of the workstation and into the "accessory storage compartment", which is the top half of the back of the workstation. This portion of the workstation can easily be accessed through the back of the workstation via a door, which can be locked. Once the cords are through the center wall and into the "accessory storage compartment" of the workstation, they are placed through another "round electrical cord portal" located at the bottom of the "accessory storage compartment" and into the "surge suppressor outlet & battery backup compartment" located in the bottom half of the back of the workstation. The "surge suppressor outlet & battery backup compartment" can also be accessed through the back of the workstation via a door, which can be locked. A single electrical cord from a hospital grade medical surge suppressor is installed through a "round electrical cord portal", which are located on both of the sidewalls of the "surge suppressor outlet & battery backup compartment", this feature allows the electrical cord to be plugged in on either side of the workstation. All of the patients' electrical medical equipment is then plugged into the medical grade surge suppressor and the surge suppressor plug is plugged into a wall outlet. The remaining length of the medical equipment electrical cords can then be neatly wound up and secured with Velcro ties hanging on the back of the center wall of the "surge suppressor outlet & battery backup compartment". The "Surge suppressor outlet and battery backup compartment" is the feature that effectively eliminates the following safety hazards caused by a patients need for multiple pieces of electrical medical equipment.

First, when a patient has four, five and six pieces of medical equipment, the electrical cords and extension cords which power the equipment create a large footprint due to a insufficient number of power outlets near a patients bed. The single patient medical workstation eliminates this problem and the cords no longer poise a trip hazard to the patient and the nurse or caregiver. Second, because the medical equipment is ultimately connected to a patient by either leads or tubing it can be accidentally unplugged from its power source by a patients movements i.e. rolling over in bed or reaching for an object. Since the power cords of the patient's equipment are locked away and concealed within the "surge suppressor & battery backup compartment" and the patients' equipment is secured within the medical equipment compartment, the likelihood of the patients equipment becoming accidentally unplugged from their power source due to patient movement is now almost impossible. Third, because many medically fragile patients require mission critical equipment such as ventilators, the single patient medical workstation is designed to house a USP system (backup battery), which shields equipment from damaging power problems and provides battery backup during blackouts, allowing patient care to continue uninterrupted. This battery backup system is housed in the "surge suppressor & battery backup compartment" of the workstation. If a patient requires a UPS system, only mission critical equipment will be plug into the battery backup system. The power cord for the UPS system will slide through a "round electrical cord portal" located on the sidewall of the 'surge suppressor and battery back compartment' and then plugged into a power outlet. The 'round electrical cord portals' are located on both the right and left side of the surge suppressor & battery backup compartment allowing the user to access the closest power source, reducing a possible trip hazard.

Medical Supplies and Medication Storage

The single patient medical workstation is designed with enough storage compartments and drawer space to easily accommodate the large quantity of immediate medical supplies needed to effectively manage the care of medically fragile patients. The fact that the workstation has the ability to store medical supplies and effectively secure medication in a locked drawer is not new concept, but the combination of this feature coupled with the other features of this invention and dedication of a single workstation to a single patient gives this invention novel features and applications beyond convention medical cabinets and storage devices. Not all medical supplies need to be secured by lock and key, but some do and all patient medication and the medical instruments used to administer that medication must be secured to prevent tempering and to effectively shutout anyone who is not authorized to administer patient medications. Many patients require large variety of medications at varying strengths, which can be extremely lethal if ingested or injected at levels other than prescribed by the physician. There are well-documented tragedies of patients, adult family members, as well as the children that have overdosed on medication that should have and could have locked away to prevent these tragedies. The problem is in a home health setting; there is currently no effective way to secure this medication at the patient's point of care, so this must be accomplished by some other means. In many case mediations is not secured at all. Patients that require this level of care have large care plans, which are preformed on a time schedule ordered by the physician and executed by a nurse or caregiver.

Drawers

All secured drawers and compartment doors on the workstation can be locked and easily accessed using a single key. The secured drawers and supply compartment doors are located directly beneath the medical equipment platform on the front side of the workstation. All of the workstations are manufactured with standard single secured medication drawer at the top of this portion of the workstation and the lower right drawer is designed to accommodate a six to eight gallon trash receptacle providing a convenient and easily accessible place to throw wipes, diapers, medical supply wrappers etc. The front wall of the trash bin drawer and the other three walls approximately four to six inches tall the canister in place.

Intravenous Pole

A specially designed Intravenous (I.V.) pole can be mounted on the left or right side of the exterior sidewalls toward the front portion of the sidewalls of the single patient medical workstation. This feature is extremely important because many medically fragile patients require I.V. therapy, infusion pumps and feeding pumps. These pieces of medical equipment are designed to utilize a combination of century old drip technology and modem pump technology and therefore must be used in concert with an I.V. pole in order to work effectively. The I.V. pole is mounted to the workstation by a simple two part mechanism system, which includes following: The vertical I.V. pole has two eight inch horizontal posts, which are welded to the vertical I.V. pole to provide a base for which the I.V. pole can be attached to the workstation. This base consists of two metal plate vertical brackets, which are welded to the ends of the two horizontal posts and are designed to set flush to the sidewall of the workstation. Each bracket has an adjustable bolt head, which slips into a keyhole slot, which is milled into the side of the workstation. The I.V. poles telescopic design can be raised to a height of about seven feet or remain lowered at a height of about five feet. When not in use the I.V. pole can be stored in the accessory storage compartment located in the back of the workstation.

Oxygen Tank Holders

Both I.V. pole and the oxygen tank holder can be mounted side by side with approximately 12 inches of separation between them. The oxygen tank holder is mounted to the workstation in the same manner as the I.V. pole but is positioned toward the back portion of the sidewall of the workstation. The design of the oxygen tank holder consists of a metal "L" shaped bar that serves as a base with two circular brackets that are attached to the bar. These circular brackets, one welded to the upper portion of the "L" shaped bar and the other at the lower portion of the "L" shaped bar secure the tank, while the "L" shaped bar bears the weight of the oxygen tank and keeps the tank from descending further than the desired depth. The positioning the oxygen tank holder on the upper sidewall of the workstation enables the nurse or caregiver to easily reach and adjust controls as well as visually read the gauges to which monitor airflow. The oxygen tank holder can be mounted on the left side or the right side of the workstation, but is normally mounted on the opposite of the slide out work tray. The oxygen tank holder can be stored in the accessory storage compartment when not in use.

Slide Out Work Tray

The slide out work tray is another unique feature of the single patient medical workstation and is designed to give a nurse or caregiver instant access to shelf/counter space. This feature provides a place to prepare medications and organize the patients medical supplies in order to carryout the physician's orders and an instant platform for which to carryout emergency procedures. The work tray can be positioned on either the right or left side of the workstation. Although dimensions can vary the typical work tray slides out approximately 15 inches for the sidewall of the workstation and is approximately 20 inches wide. The work tray is mounted on typical drawer slide rails and is positioned in the one inch space between the upper half and the lower half of the workstation. This slide rail system allows the work tray to be concealed within this one-inch space when not in use. A handle connected to the work tray allows the user to extend the work tray for use and then return the work tray to its concealed position within the workstation. The work tray handle can be secured into its concealed position by a swing latch. When the swing latch is engaged the work tray will remain in its concealed position. The handle connected to the work tray also serves as the steering mechanism when in the pulled out position (this feature will be discussed in the patient mobility section of this patent.

Patient Mobility

Patient mobility is an extremely important issue when caring medically fragile patients. Patient interaction with the rest of the family is well documented in medical journals as a factor in overall patient comfort and speed of recovery. The single patient medical workstation provides a solution to this pressing issue. The fact that medically fragile patients have so many pieces of medical equipment and supplies reduces patient mobility and usually means they are confined to a single room and are denied the opportunity to interact with the rest of the family. The fact that all of the patients equipment and supplies are in single unit allows patient and their equipment and supplies to easily be moved from room to room. It is no long necessary for nurses or caregivers to unplug and move each individual piece of equipment from one room to the other and then try to find shelf space and a sufficient number of power outlets within the room. Unplug one power cord; move the workstation where you like and plug it back in—that's it. Each workstation is mounted on four six-inch semi-pneumatic heavy-duty swivel castors, which provide maximum stability and excellent maneuverability making the single patient medical workstation highly mobile. Unplug one power cord; move it as desired and plug it back in and that is all that is necessary.

Each workstation can be pulled and maneuvered by a wooden handle located on the left and right sidewall of the workstation and secured the height between the medical equipment platform and the medical supply and medication storage compartment. The handle connected to the work tray also serves as the steering mechanism when in its pulled out position. The users hand can easily pass through each handle allowing the user the ability to maneuver the workstation with ease. On the top surface of the each handle a grove has been routered into the handle on each side of the grip allowing the user a place store writing utensils. The swing lock enable it to be move while closed, preventing the shelf from sliding out while pulling the unit. A handle in front of the unit is being implemented within the accent wood piece for future units.

Interior Light

Each single patient medical workstation is manufactured standard with a twelve-inch interior florescent light mounted to the ceiling of the workstation. This feature allows users to work under various conditions of ambient illumination at the point of care. The workstations indirect lighting enables the user to visually monitor, set and adjust controls of the medical equipment within the medical equipment platform and perform doctors orders such as administering medication and respiratory therapy while a patient is sleeping without the need for additional lighting which can shine in a patients face waking the patients from much needed rest.

The apparatus and methods of this invention provide significant advantages over the current art. The invention has been described in connection with its preferred embodiments. However, it is not limited thereto. Changes, variations and modifications to the basic design may be made without departing from the inventive concepts in this invention. In addition, these changes, variations and modifications would be obvious to those skilled in the art having the benefit of the foregoing teachings. All such changes, variations and modifications are intended to be within the scope of this invention.

I claim:

1. A method for reconfiguring a medical workstation comprising the steps of:
    determining the equipment needed for a particular patient;
    determining an amount of space required by each piece of equipment;
    designing a compartment configuration containing spaces to store each piece of equipment; and
    creating the various spaces within the compartment design using variable length dividers; and
    connecting the equipment as needed to a power source through channels in the rear of the medical workstation, by channeling wiring through an opening in an inner wall of the workstation into a back compartment; and by channeling wiring through at least one second opening in at least one middle divider such that the wiring is channeled from an upper back compartment to a lower back compartment and to the power source.

2. The method as described in claim 1 further comprising before said creating step the step of selecting the variable length dividers to be used to create the various spaces within the compartment.

3. The method as described in claim 2 wherein said creating step further comprises repositioning one or more vertical dividers contained in the medical workstation as needed to create the dimensions for the spaces that will contain the medical equipment for the patient.

4. The method as described in claim 1 further comprising the step of disassembling said workstation after completion of use for a particular patient.

5. The method as described in claim 1 further comprising the step of connecting said workstation to the proper wall connections for a hospital application.

6. The method as described in claim 1 further comprising the step placing each piece of medical equipment into the of designed compartment for that piece of equipment.

7. The method as described in claim 1 wherein the power source is within the workstation.

8. The method as described in claim 1 wherein said connecting step further comprises:
    channeling wiring out of the workstation through an opening in a back wall of the lower back compartment a power source.

9. A method for providing a medical workstation capable of being configured and reconfigured to house medical equipment comprising the steps of:
    determining medical equipment needed for a particular patient;
    designing a compartment configuration containing spaces to store each piece of equipment;
    creating the various spaces within the compartment design by selecting variable length horizontal dividers to be used to from the spaces within the compartment, positioning one or more vertical dividers in the workstation as needed to create storage spaces that will house the medical equipment for a patient and inserting the selected horizontal dividers into the workstation compartment to form the storage spaces;
    positioning the determined medical equipment in the compartment spaces; and
    connecting the medical equipment to a power source by channeling the wiring from the medical equipment to a compartment in the back of the workstation that contains an access point to a power source.

10. The method as described in claim 9 further comprising after said connecting step, the step of disassembling the configured workstation after completion of use by a particular patient and reassembling the workstation for use by another patient in accordance with said determining, designing, creating, storing and connecting steps.

11. A method for configuring and reconfiguring a medical workstation for housing medical equipment of a patient comprising the steps of:
    determining medical equipment needed for the particular patient;

designing a compartment configuration containing spaces to store each piece of equipment;

creating the various spaces within the compartment design by positioning one or more vertical dividers in the workstation as needed to create store spaces that will house the medical equipment for a patient;

positioning the determined medical equipment in the compartment spaces;

connecting the medical equipment to a power source by channeling wiring from the equipment through one or more back compartments in the medical workstation to the power source;

disassembling to workstation after completion of use for a particular patient; and reassembling the workstation for use by another patient in accordance with said determining, designing, creating, storing and connecting steps.

12. The method as described in claim 11 wherein said creating step further comprises selecting variable length horizontal dividers to be used to from the spaces within the compartment and inserting the selected horizontal dividers into the workstation compartment to form the spaces.

* * * * *